(12) United States Patent
Chattaraj et al.

(10) Patent No.: US 8,574,201 B2
(45) Date of Patent: Nov. 5, 2013

(54) SYRINGE PISTON WITH CHECK VALVE SEAL

(75) Inventors: Sarnath Chattaraj, Simi Valley, CA (US); Poonam S. Gulati, La Canada, CA (US); Lance P. Hoffman, Los Angeles, CA (US); Kiem Dang, Thousand Oaks, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 393 days.

(21) Appl. No.: 12/972,263

(22) Filed: Dec. 17, 2010

(65) Prior Publication Data

US 2011/0152785 A1 Jun. 23, 2011

Related U.S. Application Data

(60) Provisional application No. 61/289,243, filed on Dec. 22, 2009.

(51) Int. Cl.
*A61M 5/315* (2006.01)
(52) U.S. Cl.
USPC ........... 604/222; 604/221; 604/218; 604/193; 604/194; 604/219
(58) Field of Classification Search
USPC .......... 604/193–195, 187, 221–222, 218–219
See application file for complete search history.

(56) References Cited

U.S. PATENT DOCUMENTS

| | | |
|---|---|---|
| 3,631,847 A | 1/1972 | Hobbs, II |
| 4,212,738 A | 7/1980 | Henne |
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |

(Continued)

FOREIGN PATENT DOCUMENTS

| | | |
|---|---|---|
| DE | 4329229 | 3/1995 |
| EP | 242956 A1 * | 10/1987 |

(Continued)

OTHER PUBLICATIONS

PCT Search Report (PCT/US02/03299, Oct. 31, 2002, Medtronic Minimed, Inc.

(Continued)

*Primary Examiner* — Kevin C Sirmons
*Assistant Examiner* — Edelmira Bosques
(74) *Attorney, Agent, or Firm* — Ingrassia Fisher & Lorenz, P.C.

(57) ABSTRACT

A fluid syringe of the type used with fluid infusion devices is presented here. The fluid syringe generally includes a barrel, a piston, and a check valve seal. The barrel has an interior wall and a sealed main fluid chamber. The piston is slidably coupled within the barrel, and the piston has a piston seal forming an interference fluid seal against the interior wall. The check valve seal is coupled to the piston, and it is located between the piston seal and the main fluid chamber. The check valve seal forms an interference fluid seal against the interior wall when the piston is unloaded, and it disengages the interior wall to allow gas flow from the main fluid chamber toward the piston seal when the piston is loaded.

10 Claims, 8 Drawing Sheets

(56) References Cited

U.S. PATENT DOCUMENTS

| | | | |
|---|---|---|---|
| 4,433,072 A | 2/1984 | Pusineri et al. |
| 4,443,218 A | 4/1984 | DeCant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,632,672 A * | 12/1986 | Kvitrud ............... 604/222 |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,497,772 A | 3/1996 | Schulman et al. |
| 5,505,709 A | 4/1996 | Funderburk et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Iliff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,248,093 B1 | 6/2001 | Moberg |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |

(56) References Cited

U.S. PATENT DOCUMENTS

| | | |
|---|---|---|
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,396,330 B2 | 7/2008 | Banet et al. |
| 7,621,893 B2 | 11/2009 | Moberg et al. |
| 7,828,764 B2 | 11/2010 | Moberg et al. |
| 7,905,868 B2 | 3/2011 | Moberg et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |
| 2009/0299290 A1 | 12/2009 | Moberg |

FOREIGN PATENT DOCUMENTS

| | | |
|---|---|---|
| EP | 0319268 | 11/1988 |
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |
| WO | WO 2009/102355 A2 | 8/2009 |

OTHER PUBLICATIONS (Animas Corporation, 1999). Animas . . . bringing new life to insulin therapy.
Bode B W, et al. (1996). Reduction in Severe Hypoglycemia with Long-Term Continuous Subcutaneous Insulin Infusion in Type I Diabetes. Diabetes Care, vol. 19, No. 4, 324-327.
Boland E (1998). Teens Pumping it Up! Insulin Pump Therapy Guide for Adolescents. 2nd Edition.
Brackenridge B P (1992). Carbohydrate Gram Counting a Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting A Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.

(56) References Cited

OTHER PUBLICATIONS (MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.

(MiniMed Technologies, 1994). MiniMed 506 Insulin Pump User's Guide.

(MiniMed Technologies, 1994). MiniMed™ Dosage Calculator Initial Meal Bolus Guidelines / MiniMed™ Dosage Calculator Initial Basal Rate Guidelines Percentage Method. 4 pages.

(MiniMed, 1996). MiniMed™ 507 Insulin Pump User's Guide.

(MiniMed, 1997). MiniMed™ 507 Insulin Pump User's Guide.

(MiniMed, 1998). MiniMed 507C Insulin Pump User's Guide.

(MiniMed International, 1998). MiniMed 507C Insulin Pump for those who appreciate the difference.

(MiniMed Inc., 1999). MiniMed 508 Flipchart Guide to Insulin Pump Therapy.

(MiniMed Inc., 1999). Insulin Pump Comparison / Pump Therapy Will Change Your Life.

(MiniMed, 2000). MiniMed® 508 User's Guide.

(MiniMed Inc., 2000). MiniMed® Now [I] Can Meal Bolus Calculator / MiniMed® Now [I] Can Correction Bolus Calculator.

(MiniMed Inc., 2000). Now [I] Can MiniMed Pump Therapy.

(MiniMed Inc., 2000). Now [I] Can MiniMed Diabetes Management.

(Medtronic MiniMed, 2002). The 508 Insulin Pump a Tradition of Excellence.

(Medtronic MiniMed, 2002). Medtronic MiniMed Meal Bolus Calculator and Correction Bolus Calculator. International Version.

Abel, P., et al., "Experience with an implantable glucose sensor as a prerequiste of an artificial beta cell," Biomed. Biochim. Acta 43 (1984) 5, pp. 577-584.

Bindra, Dilbir S., et al., "Design and in Vitro Studies of a Needle-Type Glucose Sensor for a Subcutaneous Monitoring," American Chemistry Society, 1991, 63, pp. 1692-1696.

Boguslavsky, Leonid, et al., "Applications of redox polymers in biosensors," Sold State Ionics 60, 1993, pp. 189-197.

Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.

Gernet, S., et al., "A Planar Glucose Enzyme Electrode," Sensors and Actuators, 17, 1989, pp. 537-540.

Gernet, S., et al., "Fabrication and Characterization of a Planar Electromechanical Cell and its Application as a Glucose Sensor," Sensors and Actuators, 18, 1989, pp. 59-70.

Gorton, L., et al., "Amperometric Biosensors Based on an Apparent Direct Electron Transfer Between Electrodes and Immobilized Peroxiases," Analyst, Aug. 1991, vol. 117, pp. 1235-1241.

Gorton, L., et al., "Amperometric Glucose Sensors Based on Immobilized Glucose-Oxidizing Enymes and Chemically Modified Electrodes," Analytica Chimica Acta, 249, 1991, pp. 43-54.

Gough, D. A., et al., "Two-Dimensional Enzyme Electrode Sensor for Glucose," Analytical Chemistry, vol. 57, No. 5, 1985, pp. 2351-2357.

Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.

Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.

Heller, Adam, "Electrical Wiring of Redox Enzymes," Acc. Chem. Res., vol. 23, No. 5, May 1990, pp. 128-134.

Jobst, Gerhard, et al., "Thin-Film Microbiosensors for Glucose-Lactate Monitoring," Analytical Chemistry, vol. 68, No. 18, Sep. 15, 1996, pp. 3173-3179.

Johnson, K.W., et al., "In vivo evaluation of an electroenzymatic glucose sensor implanted in subcutaneous tissue," Biosensors & Bioelectronics, 7, 1992, pp. 709-714.

Jönsson, G., et al., "An Electromechanical Sensor for Hydrogen Peroxide Based on Peroxidase Adsorbed on a Spectrographic Graphite Electrode," Electroanalysis, 1989, pp. 465-468.

Kanapieniene, J. J., et al., "Miniature Glucose Biosensor with Extended Linearity," Sensors and Actuators, B. 10, 1992, pp. 37-40.

Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.

Kimura, J., et al., "An Immobilized Enzyme Membrane Fabrication Method," Biosensors 4, 1988, pp. 41-52.

Koudelka, M., et al., "In-vivo Behaviour of Hypodermically Implanted Microfabricated Glucose Sensors," Biosensors & Bioelectronics 6, 1991, pp. 31-36.

Koudelka, M., et al., "Planar Amperometric Enzyme-Based Glucose Microelectrode," Sensors & Actuators, 18, 1989, pp. 157-165.

Mastrototaro, John J., et al., "An electroenzymatic glucose sensor fabricated on a flexible substrate," Sensors & Actuators, B. 5, 1991, pp. 139-144.

Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.

McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.

Monroe, D., "Novel Implantable Glucose Sensors," ACL, Dec. 1989, pp. 8-16.

Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.

Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.

Nakamoto, S., et al., "A Lift-Off Method for Patterning Enzyme-Immobilized Membranes in Multi-Biosensors," Sensors and Actuators 13, 1988, pp. 165-172.

Nishida, Kenro, et al., "Clinical applications of teh wearable artifical endocrine pancreas with the newly designed needle-type glucose sensor," Elsevier Sciences B.V., 1994, pp. 353-358.

Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.

Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in (56) References Cited

OTHER PUBLICATIONS

Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

* cited by examiner

SYRINGE PISTON WITH CHECK VALVE SEAL

CROSS-REFERENCE TO RELATED APPLICATION(S)

This application claims the benefit of U.S. provisional patent application Ser. No. 61/289,243, filed Dec. 22, 2009.

TECHNICAL FIELD

Embodiments of the subject matter described herein relate generally to syringes and syringe pistons of the type used to deliver fluids, such as medication. More particularly, embodiments of the subject matter relate to a syringe piston having a check valve seal.

BACKGROUND

Portable medical devices are useful for patients that have conditions that must be monitored on a continuous or frequent basis. For example, diabetics are usually required to modify and monitor their daily lifestyle to keep their body in balance, in particular, their blood glucose (BG) levels. Individuals with Type 1 diabetes and some individuals with Type 2 diabetes use insulin to control their BG levels. To do so, diabetics routinely keep strict schedules, including ingesting timely nutritious meals, partaking in exercise, monitoring BG levels daily, and adjusting and administering insulin dosages accordingly.

The prior art includes a number of fluid infusion devices and insulin pump systems that are designed to deliver accurate and measured doses of insulin via infusion sets (an infusion set delivers the insulin through a small diameter tube that terminates at, e.g., a cannula inserted under the patient's skin). In lieu of a traditional syringe, the patient can simply activate the insulin pump to administer an insulin bolus as needed, for example, in response to the patient's current BG level.

A typical infusion pump includes a housing, which encloses a pump drive system, a fluid containment assembly, an electronics system, and a power supply. The pump drive system typically includes a small motor (DC, stepper, solenoid, or other varieties) and drive train components such as gears, screws, and levers that convert rotational motor motion to a translational displacement of a piston in a reservoir, which may be in the form of a user-filled syringe or a pre-filled syringe. The fluid containment assembly typically includes the reservoir with the piston, tubing, and a catheter or infusion set to create a fluid path for carrying medication from the reservoir to the body of a user. The electronics system regulates power from the power supply to the motor. The electronics system may include programmable controls to operate the motor continuously or at periodic intervals to obtain a closely controlled and accurate delivery of the medication over an extended period.

The presence of air bubbles in a fluid syringe is undesirable for various reasons. Accordingly, air inside of user-filled syringes is usually expelled before the syringe is used. Moreover, air might be introduced into a pre-filled syringe during the filling and sealing processes. Therefore, various manufacturing techniques are implemented in an attempt to remove air from pre-filled syringes before sealing and/or to minimize the amount of air that gets introduced into the fluid. In this regard, conventional approaches often rely on vacuum filling and/or vacuum stoppering to remove or reduce the amount of air that gets trapped in the pre-filled syringes. Such techniques, however, involve specialized equipment, require additional handling of the product, and result in lower throughput.

Accordingly, it is desirable to have a different methodology for handling gas trapped inside of a fluid syringe. In addition, it is desirable to have a syringe piston design and a related syringe piston that can be manipulated to manage the presence of gas inside of the fluid chamber.

BRIEF SUMMARY

An exemplary embodiment of a syringe piston is provided. The syringe piston includes a piston body having a fluid end and an actuator end opposite the fluid end, and a piston seal coupled to the piston body and located between the fluid end and the actuator end. The piston seal forms an interference fluid seal with an interior wall of a syringe barrel. The syringe piston also includes a check valve seal coupled to the piston body and positioned such that the piston seal is located between the check valve seal and the actuator end, and a gas entrapment zone defined between the check valve seal and the piston seal. The check valve seal allows one-way gas flow into the gas entrapment zone.

Also provided is an exemplary embodiment of a fluid syringe. The fluid syringe includes a syringe barrel comprising an interior wall and a sealed main fluid chamber, a syringe piston slidably coupled within the syringe barrel, and a check valve seal coupled to the syringe piston and located between the piston seal and the main fluid chamber. The syringe piston includes a piston seal forming an interference fluid seal against the interior wall. The check valve seal forms an interference fluid seal against the interior wall when the syringe piston is unloaded, and the check valve seal disengages the interior wall to allow gas flow from the main fluid chamber toward the piston seal when the syringe piston is loaded.

An exemplary embodiment of a method of manufacturing a fluid syringe is also provided. The method involves the fabrication of a syringe assembly having a syringe barrel having an interior wall and a main fluid chamber, a sealing cap having a penetrable membrane, a syringe piston slidably coupled within the syringe barrel and partially defining the main fluid chamber, and a liquid within the main fluid chamber. The syringe piston includes a piston seal forming an interference fluid seal against the interior wall, and a check valve seal located between the piston seal and the main fluid chamber. The method continues by maintaining the syringe assembly in a position that allows gas in the main fluid chamber to accumulate and rise toward the syringe piston and, after the gas in the main fluid chamber has settled at the check valve seal, applying a force to the syringe piston to move the syringe piston into the syringe barrel while maintaining the syringe assembly in the position. The check valve seal allows the gas to flow from the main fluid chamber into an entrapment zone defined between the piston seal, the check valve seal, and the interior wall. After the gas flows past the check valve seal into the entrapment zone, the method removes the force from the syringe piston to return the check valve seal to an unbiased state, such that the check valve seal retains the gas in the entrapment zone.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "upper", "lower", "above", and "below" refer to directions in the drawings to which reference is made. Terms such as "front", "back", "rear", "side", "outboard," and "inboard" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

The subject matter presented here relates to a check valve seal for a piston that is used to deliver a fluid (such as a liquid medication) from a fluid syringe to a person. Although the check valve seal concept can be utilized with user-filled syringes or pre-filled syringes, certain benefits described herein apply to pre-filled syringes that do not easily accommodate the expulsion of trapped air by the user. Accordingly, the following description focuses on pre-filled syringe embodiments. Moreover, the following description relates to a fluid infusion device of the type used to treat a medical condition of a patient. The infusion device is used for infusing fluid into the body of a user. The non-limiting examples described below relate to a medical device used to treat diabetes (more specifically, an insulin pump), although embodiments of the disclosed subject matter are not so limited. Accordingly, the infused fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For or the sake of brevity, conventional features and characteristics related to infusion system operation, insulin pump and/or infusion set operation, fluid reservoirs, and fluid syringes may not be described in detail here. Examples of infusion pumps and/or related pump drive systems used to administer insulin and other medications may be of the type described in, but not limited to, United States patent application number 2009/0299290 A1 (the content of which is incorporated by reference in its entirety herein).

The check valve seal and the syringe assembly described here facilitate the containment of entrapped air, which may be introduced or created during the syringe filling process of a pre-filled syringe (after piston seating in the syringe barrel). Some conventional syringe pistons include two seals designed to protect the syringe-filled solutions from environmental conditions. A syringe with the two-seal design might contain solution and air within the syringe after piston installation. Air entrapped in the syringe is only vented by inverting the syringe and expelling a small quantity of solution/air mixture prior to needle injection.

In contrast to conventional syringe designs, the syringe piston described here includes an additional seal (the check valve seal) that faces the fluid chamber. The check valve seal is constructed to serve as a mechanical check valve between the syringe solution and the other piston seals. When positioned upright (i.e., the piston end of the syringe up), the entrapped air in the syringe will rise to the piston base. Thereafter, the piston is engaged (moved toward the solution in the fluid chamber) while the tip of the syringe is sealed. This mode of piston engagement allows entrapped solution/air to pass by the check valve seal into a cavity of the syringe, thereby containing the air and keeping the air out of the syringe solution. The check valve is designed to eliminate backflow of the solution/air mixture from the containment cavity to the syringe solution. Thus, when the syringe is capped or sealed, the check valve seal can be manipulated like a flap to accommodate fluid flow in one direction while inhibiting fluid flow in the other direction.

Figure 1:
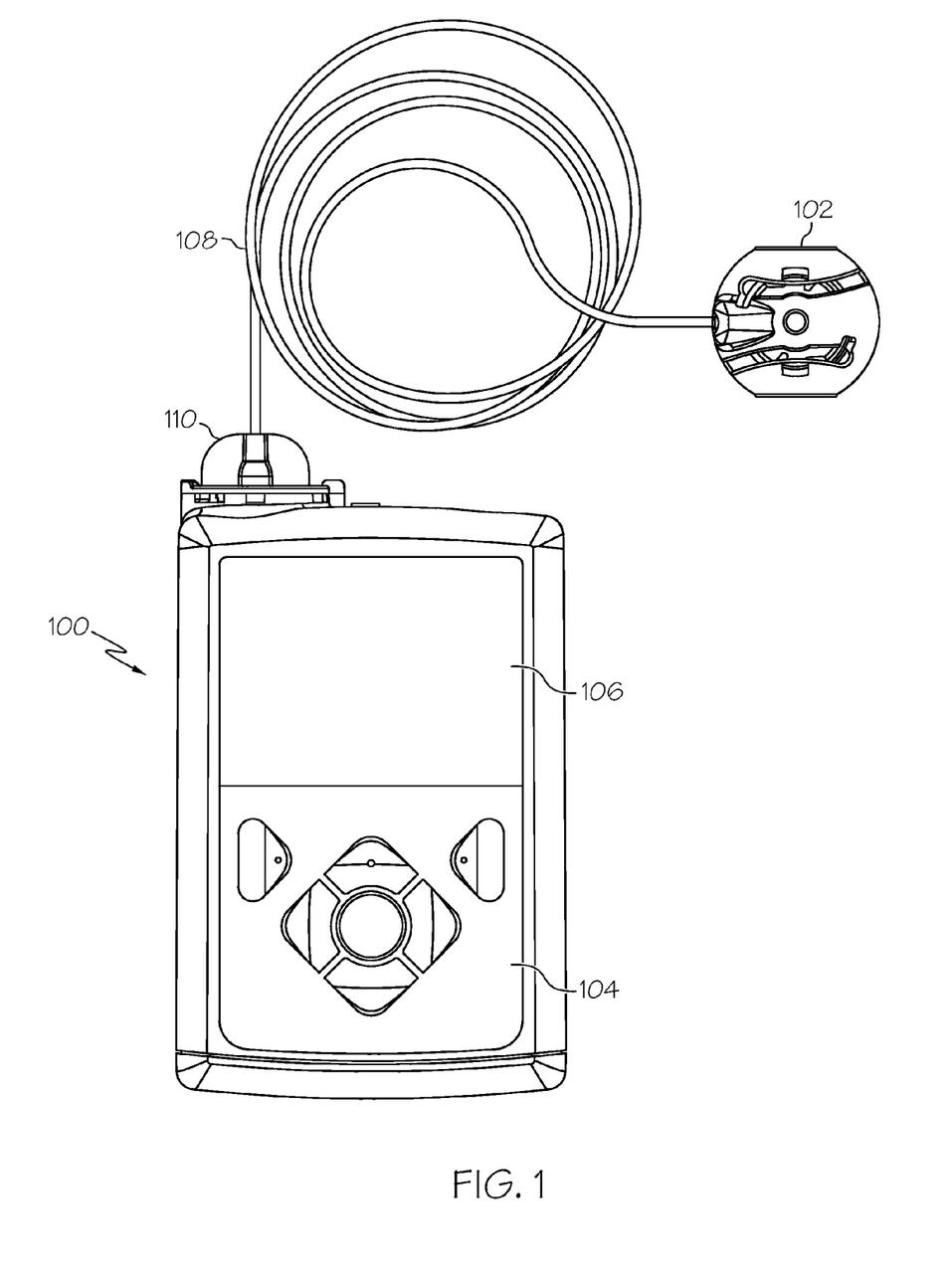
FIG. 1 is a schematic representation of an embodiment of a fluid infusion device.
Figure 2:
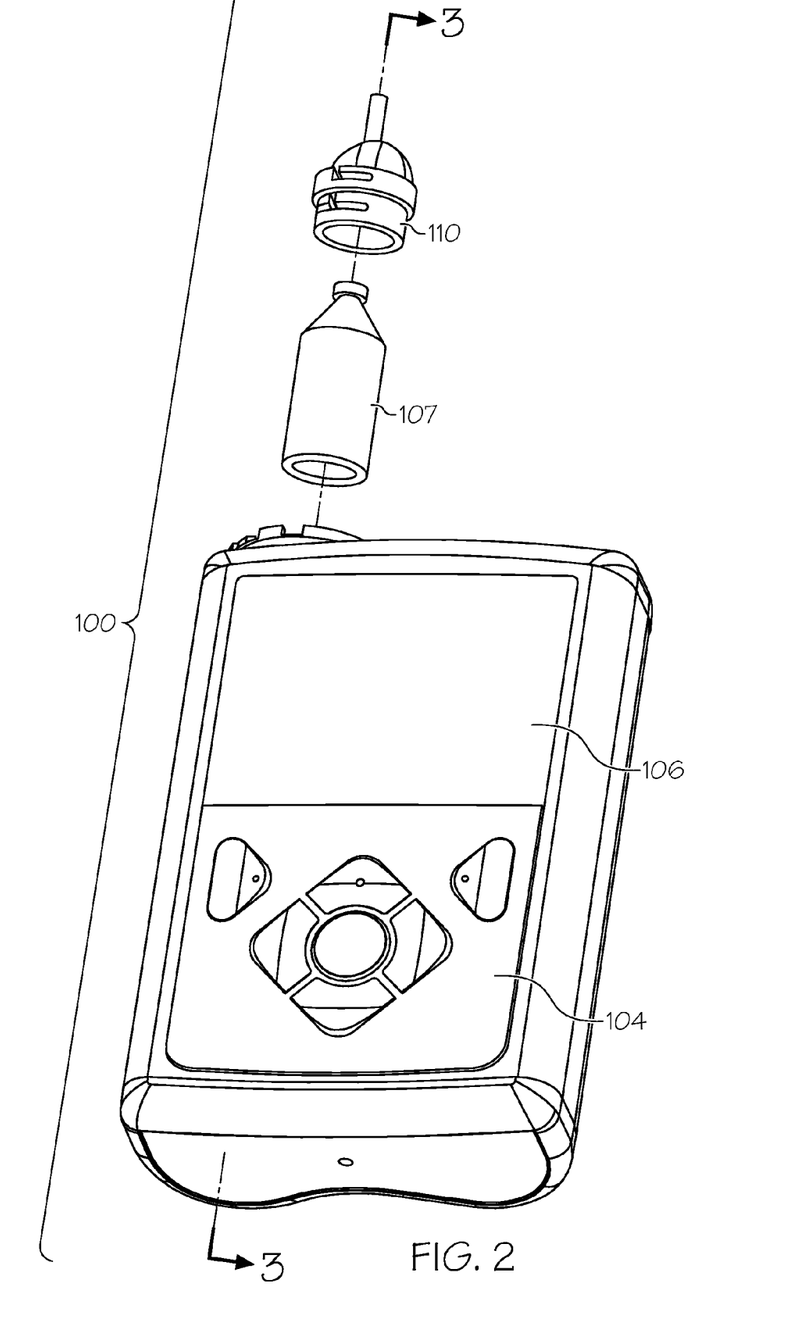
FIG. 2 is an exploded perspective view of the fluid infusion device shown in FIG. 1.

Referring now to the drawings, FIG. 1 is a schematic representation of an embodiment of a fluid infusion device 100, and FIG. 2 is an exploded perspective view of the fluid infusion device 100. FIG. 1 also shows an infusion set 102 coupled to the fluid infusion device 100. The fluid infusion device 100 is designed to be carried or worn by the patient. The fluid infusion device 100 may leverage a number of conventional features, components, elements, and characteristics of conventional and well known fluid infusion devices. For example, the fluid infusion device 100 may incorporate some of the features, components, elements, and/or characteristics described in U.S. Pat. Nos. 6,485,465 and 7,621,893, the relevant content of which is incorporated by reference herein.

Referring to FIG. 1, the fluid infusion device 100 includes a user interface 104 that includes several buttons that can be activated by the user. These buttons can be used to administer a bolus of insulin, to change therapy settings, to change user preferences, to select display features, and the like. Although not required, the illustrated embodiment of the fluid infusion device 100 includes a display element 106. The display element 106 can be used to present various types of information or data to the user, such as, without limitation: the current glucose level of the patient; the time; a graph or chart of the patient's glucose level versus time; device status indicators; etc. In some embodiments, the display element 106 is realized as a touch screen display element and, therefore, the display element 106 also serves as a user interface component.

The fluid infusion device 100 accommodates a fluid syringe 107 (see FIG. 2) for the fluid to be delivered to the user. Note that the words "syringe" and "reservoir" are used interchangeably herein; both refer to a fluid containment component that can be actuated to dispense fluid. A length of tubing 108 fluidly couples the fluid syringe 107 to the infusion set 102. The tubing 108 extends from the fluid infusion device 100 to the infusion set 102, which provides fluid communication with the body of the user. A removable cap or fitting 110 is suitably sized and configured to accommodate replacement of fluid reservoirs (which are typically disposable) as needed. In this regard, the fitting 110 is designed to accommodate the fluid path from the fluid syringe 107 to the tubing 108.

Figure 3:
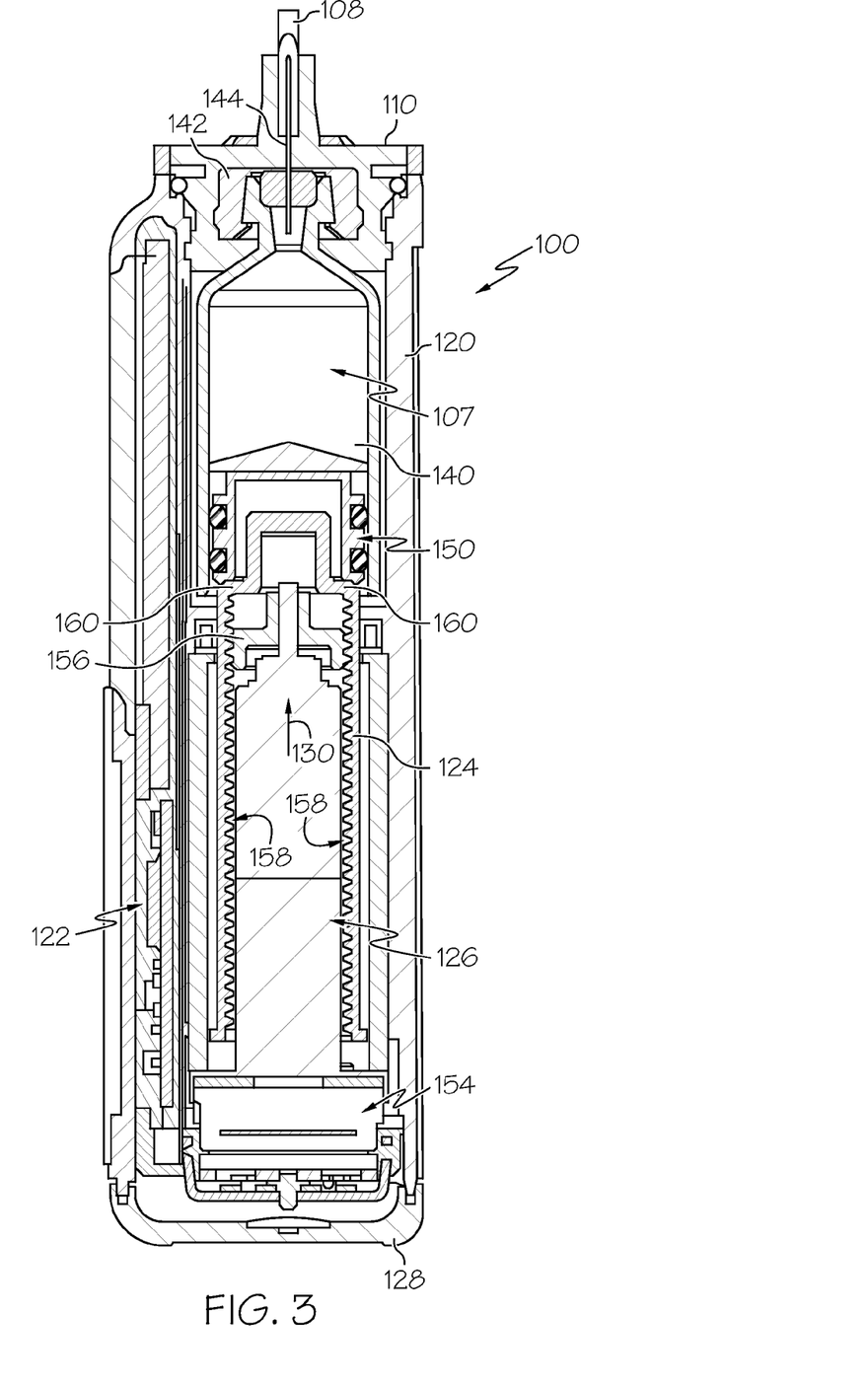
FIG. 3 is a cross-sectional view of the fluid infusion device (as viewed along line 3-3 in FIG. 2) with a fluid syringe installed therein.

FIG. 3 is a cross-sectional view of the fluid infusion device 100 with the fluid syringe 107 installed therein. The illustrated embodiment of the fluid infusion device 100 includes, without limitation: a housing 120; an electronics assembly 122; a slide 124; and a drive system 126. The housing 120 includes an opening adapted to receive the fluid syringe 107. FIG. 3 illustrates the relationship between the drive system 126, the slide 124, and the fluid syringe 107. FIG. 3 shows other components and features that are conventional in nature and/or are unrelated to the subject matter presented here. Moreover, it should be appreciated that FIG. 3 depicts the fluid infusion device 100 in a simplified manner. In practice, the fluid infusion device 100 could include additional elements, features, or components that are not shown or described in detail here.

The housing 120 has a hollow interior that accommodates the electronics assembly 122, the fluid syringe 107, the slide 124, and the drive system 126, which are enclosed within the housing 120 by a bottom portion 128. In the illustrated embodiment, the slide 124, the drive system 126, and the fluid syringe 107 are aligned in an axial direction (indicated by arrow 130). As described in greater detail below, the drive system 126 facilitates displacement of the slide 124 in the axial direction 130 to dispense fluid from the fluid syringe 107.

The electronics assembly 122 includes control electronics that generally represent the hardware, firmware, processing logic and/or software (or combinations thereof) to control operation of the drive system 126 and other features of the fluid infusion device 100. In an exemplary embodiment, the electronics assembly 122 includes one or more programmable controllers that may be programmed to control the various operations of the fluid infusion device 100.

Depending on the embodiment, the fluid syringe 107 may be realized as a disposable reservoir, a user-filled reservoir, a pre-filled reservoir, a vial, a cartridge, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. The fluid syringe 107 typically includes a barrel 140 that contains the fluid and is concentrically and/or coaxially aligned with the slide 124 (e.g., in the axial direction 130) when the fluid syringe 107 is installed in the fluid infusion device 100. The fluid delivery end of the fluid syringe 107 may include a suitably configured sealing cap 142 that cooperates with the fitting 110 in a way that allows the fitting 110 to secure the fluid syringe 107 in the housing 120. When the fitting 110 is in place (as depicted in FIG. 3), displacement of the fluid syringe 107 in the axial direction 130 is inhibited. In an exemplary embodiment, the sealing cap 142 includes a penetrable membrane that is punctured by a delivery needle 144 of the fitting 110. In this manner, the fitting 110 secures the fluid syringe 107 within the housing 120 and also serves to secure and connect the fluid syringe 107 to the infusion set tubing 108.

The base end of the fluid syringe 107 (which is near the slide 124) includes a syringe piston 150 positioned to push fluid from inside the barrel 140 of the fluid syringe 107 along a fluid path through the tubing 108 to a user. Note that the words "piston," "stopper," and "plunger" may be used interchangeably herein; these words all refer to the component that moves within the fluid syringe 107 to dispense fluid from the barrel 140. The slide 124 is configured to mechanically couple or otherwise engage with the piston 150, thereby becoming seated with the piston 150. In operation, fluid is forced from the fluid syringe 107 via the tubing 108 as the drive system 126 is actuated to displace the slide 124 in the axial direction 130 toward the sealing cap 142.

In an exemplary embodiment, the drive system 126 includes a motor assembly 154 and a drive screw 156. The motor assembly 154 might include a motor and associated drive train components that convert rotational motor motion to a translational displacement of the slide 124 in the axial direction 130, thereby engaging and displacing the piston 150 of the fluid syringe 107. In some embodiments, the motor assembly 154 may also be powered to rewind the slide 124 in the opposing direction to accommodate removal and replacement of the fluid syringe 107. Although the illustrated embodiment of the fluid infusion device 100 utilizes a coaxially aligned drive system 126, the motor assembly 154 could instead be arranged in an offset or otherwise non-coaxial manner, relative to the longitudinal axis of the fluid syringe 107.

The drive screw 156 mates with internal threads 158 internal to the slide 124. When the motor assembly 154 is powered, the drive screw 156 rotates, and the slide 124 is forced to translate in the axial direction 130. In an exemplary embodiment, the fluid infusion device 100 includes a feature that prevents the slide 124 from rotating when the drive screw 156 rotates. Thus, rotation of the drive screw 156 causes the slide 124 to extend or retract relative to the motor assembly 154. When the fluid infusion device 100 is assembled and operational, the slide 124 contacts the piston 150 to engage the fluid syringe 107 and to control delivery of fluid from the fluid infusion device 100. In an exemplary embodiment, a shoulder portion 160 of the slide 124 contacts or otherwise engages the piston 150 to displace the piston 150 in the axial direction 130. In alternative embodiments (not shown), the slide 124 may include a threaded tip capable of being detachably engaged with internal threads formed in the piston 150, as described in detail in U.S. Pat. Nos. 6,248,093 and 6,485,465, which are incorporated by reference herein.

Figure 4:
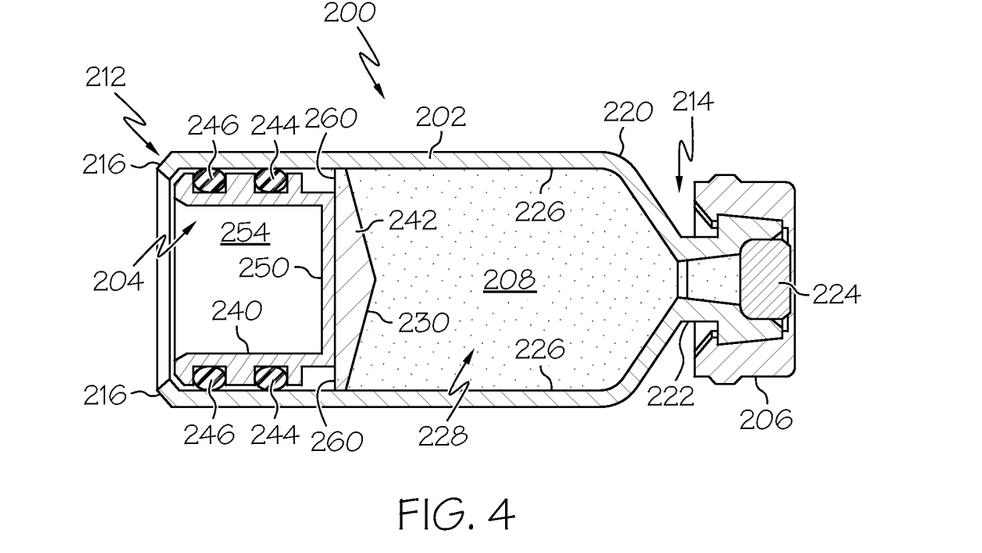
FIG. 4 is a cross-sectional view of an exemplary embodiment of a fluid syringe, taken along its major longitudinal axis.

FIG. 4 is a cross sectional view of an exemplary embodiment of a fluid syringe 200, taken along its major longitudinal axis. Note that the fluid syringe 200 could be used as one suitable embodiment of the fluid syringe 107 shown in FIG. 2 and FIG. 3. This particular embodiment of the fluid syringe 200 is a pre-filled component, and FIG. 4 depicts the fluid syringe 200 in its pre-filled state prior to use and prior to installation into a fluid infusion device. The fluid syringe 200 generally includes, without limitation: a body or barrel 202; a piston 204; a sealing cap 206; and fluid 208 contained in the barrel 202. For this example, the fluid 208 is a liquid medication such as insulin.

The barrel 202 can be formed from plastic, metal, glass, or the like. The barrel 202 has a base end 212 and a cap end 214 opposite the base end 212. The base end 212 may include or cooperate with a retaining feature 216 that is designed to retain the piston 204 within the barrel 202. The retaining feature 216 prevents the piston 204 from slipping out of the barrel 202 during manufacturing, shipping, storage, and handling of the fluid syringe 200. The retaining feature 216 could be realized as an inward protruding rim or shoulder (as depicted in FIG. 4), as one or more keyway features, as a separate ring or other securing component that can be coupled to the fluid syringe 200, or the like. The cap end 214 of the barrel 202 has a generally conical-shaped portion 220 which tapers to a neck region 222. The sealing cap 206 is installed onto the neck region 222, thereby forming a fluid-tight seal. In accordance with conventional reservoir designs, the sealing cap 206 includes a penetrable membrane 224 or an insert that can be pierced by a dispensing needle (as described above with reference to FIG. 3). The penetrable membrane 224 may also be referred to as a "septum." The penetrable membrane 224 is designed to preserve its seal after it is pierced, to minimize leakage of fluid around the dispensing needle.

The barrel 202 has an interior wall 226 that defines a main fluid chamber 228 of the barrel 202. As shown in FIG. 4, the fluid 208 resides within the main fluid chamber 228. The main fluid chamber 228 is sealed after the fluid syringe 200 is filled with the fluid 208; FIG. 4 depicts the main fluid chamber 228 in its sealed state. The end surface 230 of the piston 204 also defines the main fluid chamber 228, which changes volume as the piston 204 is moved within the barrel 202.

The piston 204 is slidably coupled within the barrel 202, such that actuation of the piston 204 results in the delivery of the fluid 208 (when the main fluid chamber 228 is unsealed, for example, by piercing the membrane 224). The piston 204 is suitably designed to form a fluid-tight barrier within the barrel 202 such that the fluid 208 does not leak from the base end 212 of the fluid syringe 200 and such that contaminants do not enter the main fluid chamber 228. This particular embodiment of the piston 204 includes, without limitation: a piston body 240; a check valve seal 242; a piston seal 244; and an end seal 246. The end seal 246 may be realized as a second piston seal, or, in certain embodiments, the piston seal 244 and the end seal 246 may be one and the same. In yet other embodiments, three or more seals could be used with the check valve seal 242.

The piston body 240 can be formed from plastic, metal, glass, or the like. The piston body 240 has a fluid end 250 and an actuator end 252 opposite the fluid end 250. When the piston 204 is installed in the barrel 202, the fluid end 250 is near the main fluid chamber 228. The piston body 240 has a cavity 254 defined therein. The cavity 254 is shaped and sized to receive an actuation component, such as the tip of the slide 124 shown in FIG. 3. The exterior of the piston body 240 includes a number of features that accommodate the check valve seal 242, the piston seal 244, and/or the end seal 246. In this regard, the exterior of the piston body 240 may include one or more of the following features or elements (formed therein, attached thereto, or coupled thereto), without limitation: ridges; shoulders; flanges; protrusions; cavities; rims; slots; holes; seats; grooves; and contours. For the embodiment illustrated in FIG. 4, the piston body 240 includes one circumferential groove that accommodates and retains the end seal 246 and another circumferential groove that accommodates and retains the piston seal 244. The piston body 240 may also include another groove or other feature for the check valve seal 242. The illustrated embodiment, however, includes a check valve seal 242 that is mounted atop the piston body 240 such that the major outer surface of the check valve seal 242 faces the fluid 208. Depending on its design, the check valve seal 242 could be coupled to the piston body 240 by way of a press-fit or snap-fit engagement.

The end seal 246 is coupled to the piston body 240 near the actuator end 252, the check valve seal 242 is coupled to the piston body 240 near the fluid end 250, and the piston seal 244 is coupled to the piston body 240 at a location between the fluid end 250 and the actuator end 252. More specifically, the piston seal 244 is positioned between the check valve seal 242 and the end seal 246, as shown in FIG. 4. The piston seal 244 is formed from a suitable material or composition that enables the piston seal 244 to form an interference fluid seal with the interior wall 226 of the barrel 202. In this regard, the piston seal 244 is preferably formed from a resilient and pliable material such as rubber, plastic, urethane, or the like. In certain embodiments, the piston seal 244 is realized as a rubber o-ring that is coupled around the piston body 240. The end seal 246 may be configured as described above for the piston seal 244 and, indeed, the end seal 246 is identical to the piston seal 244 in some embodiments.

When the piston 204 is installed in the barrel 202, the check valve seal 242 forms an interference fluid seal against the interior wall 226 when the piston 204 is unloaded (i.e., no force is applied to the piston 204). FIG. 4 depicts the check valve seal 242 in this nominal state. In certain embodiments, the check valve seal 242 includes a flap 260 that forms the interference fluid seal with the interior wall 226. As explained below, the flap 260 is intentionally designed with asymmetric deflection characteristics. More specifically, the flap 260 is shaped, sized, and otherwise configured such that it is easier to deflect in the direction toward the actuator end 252, and such that it is difficult to deflect in the direction away from the actuator end 252. In other words, the flap 260 functions as a one-way fluid flow regulator. For this embodiment, the check valve seal 242 is tapered such that it is thinner at its outer perimeter (near the barrel 202). In this regard, the check valve seal 242 may resemble an arrowhead.

In practice, the check valve seal 242 is preferably formed from a resilient and pliable material such as rubber, plastic, urethane, or the like. In certain embodiments, the check valve seal 242 is formed from a material or composition that is different than that used for the piston seal 244 and the end seal 246. In this regard, the piston seal 244 and the end seal 246 may be formed from a resilient material having a first durometer, and the check valve seal 242 may be formed from a different resilient material having a second durometer (e.g., the second durometer is higher than the first durometer). Alternatively, the durometer of the piston seal 244 may be equal to the durometer of the check valve seal 242. Consequently, the static, dynamic, and structural properties of the material used for the check valve seal 242 might be different than the static, dynamic, and structural properties of the material used for the piston seal 244 and the end seal 246.

Figure 5:
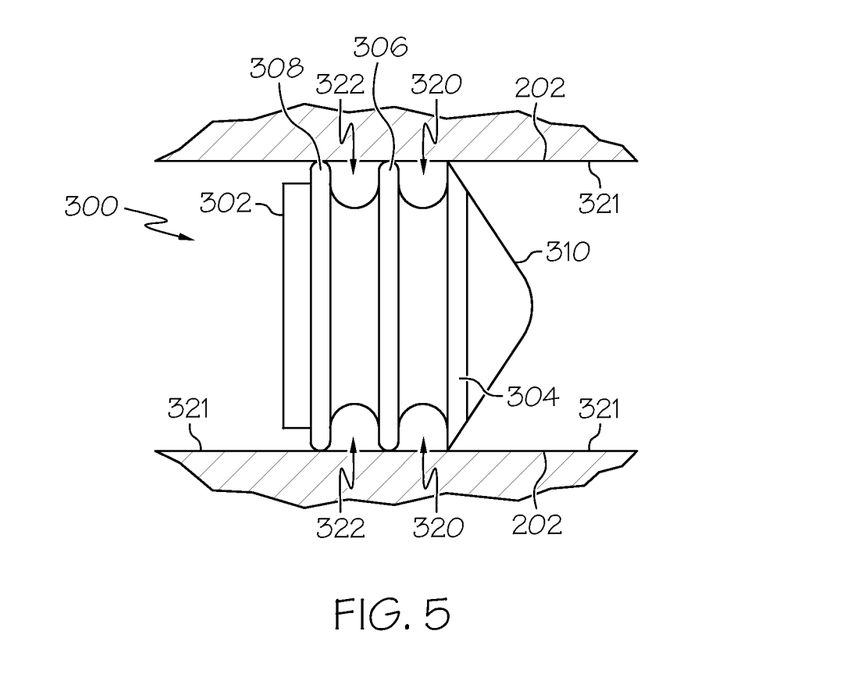
FIG. 5 is a side view of an exemplary embodiment of a syringe piston that is suitable for use with the fluid syringe shown in FIG. 3.

FIG. 5 is a side view of an exemplary embodiment of a syringe piston 300 that is suitable for use with the fluid syringe 200. Many of the features and characteristics of the piston 300 are identical or similar to that described above for the piston 204. Accordingly, common features and aspects of the pistons 204, 300 will not be described in detail here. This embodiment of the piston 300 generally includes, without limitation: a piston body 302; a check valve seal 304; a piston seal 306; and an end seal 308. As described above for the piston 204, the piston seal 306 and the end seal 308 fit within respective grooves formed in the exterior of the piston body 302. Piston 300 also employs a third groove for the check valve seal 304. Thus, the check valve seal 304 may be realized as a ring-shaped seal that is stretched or otherwise manipulated for installation into its retaining groove. In this regard, the fluid end 310 of the piston body 302 is located above the check valve seal 304. This particular embodiment of the check valve seal 304 exhibits a sloped and angled profile, such that its perimeter is very thin at the point of contact with the barrel 202. Notably, the surface of the check valve seal 304 that faces the main fluid chamber slopes downward toward the barrel 202 and toward the end seal 308, as shown in FIG. 5. Of course, the shape, size, and profile of the check valve seal 304 could vary from that shown here.

The pistons 204, 300 are suitably configured with various fluid, gas, and/or buffer zones or chambers defined between the different seals. As best shown in FIG. 5, the piston 300 includes a fluid entrapment zone 320 defined between the check valve seal 304, the piston seal 306, and the interior wall 321 of the barrel 202. In typical implementations, the fluid entrapment zone 320 is utilized as a collection and retention chamber for unwanted air or other gas that might be present after filling the fluid syringe. As described in more detail below, under certain conditions the check valve seal 304 allows one-way fluid flow into the fluid entrapment zone 320 when the syringe piston 300 is installed in the barrel 202. In this regard, when the fluid syringe is deployed and unsealed for purposes of dispensing fluid, the check valve seal 304 forms an interference fluid seal against the interior wall 321 of the barrel 202 and inhibits or prevents fluid flow from the fluid entrapment zone 320 into the main fluid chamber within the barrel 202.

The piston 300 may also include a buffer zone 322 or chamber defined between the piston seal 306, the end seal 308, and the interior wall 321 of the barrel 202. The buffer zone 322 is helpful to inhibit or prevent the incursion of outside contaminants or moisture into the main fluid chamber within the barrel 202. In certain embodiments, the piston seal 306 inhibits or prevents fluid flow from the fluid entrapment zone 320 toward the end seal 308. In other words, the piston seal 306 inhibits or prevents fluid flow from the fluid entrapment zone 320 into the buffer zone 322.

Figure 6:
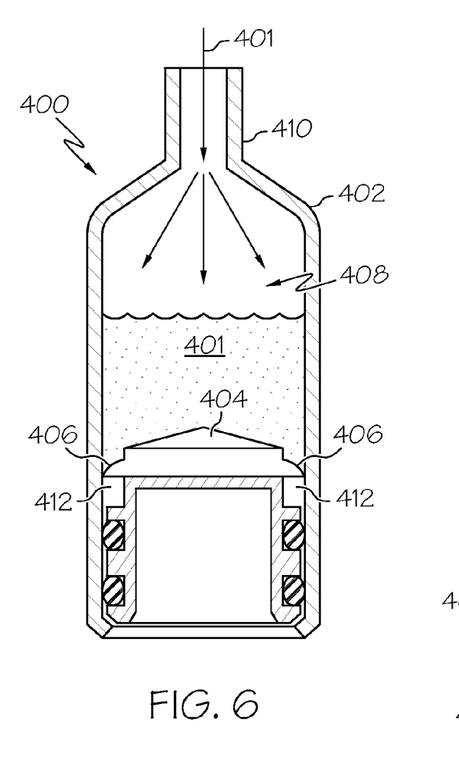
FIGS. 6-10 are diagrams that illustrate a fluid syringe and a method of manufacturing it.

The check valve seals 242, 304 described here facilitate the handling of air or other gas that might become trapped in a pre-filled fluid syringe during manufacturing. In this regard, FIGS. 6-10 are diagrams that illustrate an exemplary embodiment of a fluid syringe and an exemplary method of manufacturing it. FIG. 6 depicts a syringe assembly 400 as it is being filled with a liquid 401. The syringe assembly 400 includes a barrel 402, a piston 404, and a check valve seal 406 having the features and characteristics described above. The piston 404 is depicted in a simplified schematic form in FIGS. 6-10 for the sake of clarity.

Figure 7:
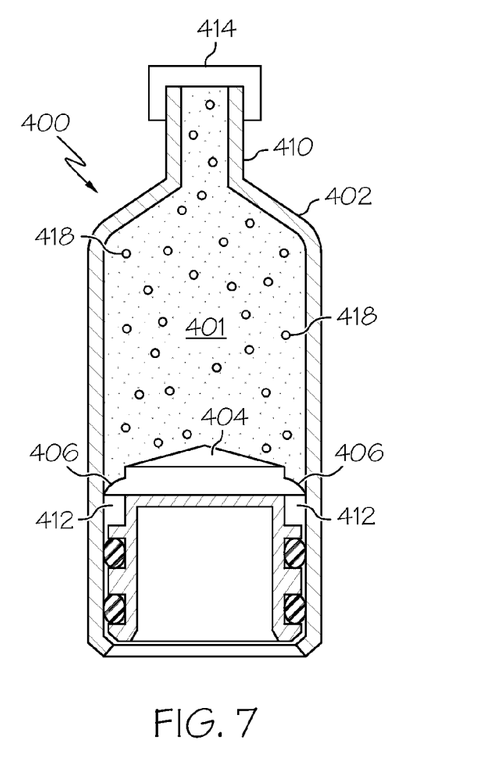

As shown in FIG. 6, the main fluid chamber 408 is filled by dispensing the liquid 401 into the neck region 410 of the barrel 402, which is open or uncapped. In practice, the piston 404 is positioned at or near the bottom of the barrel 402 during the filling operation. This position (shown in FIG. 6) may be considered to be the filling position of the piston 404. The check valve seal 406 cooperates with and seals against the interior wall of the barrel 402 while the liquid 401 is dispensed into the barrel 402. Consequently, the liquid 401 remains above the check valve seal 406 and it does not leak into the fluid containment zone 412. The liquid 401 is dispensed into the neck region 410 until the barrel 402 is filled. Thereafter, the manufacturing process may install a sealing cap 414 onto the neck region 410 to seal the liquid 401 inside the barrel 402 (see FIG. 7). At this time, the barrel 402 and the main fluid chamber are closed (sealed) and the piston 404 is unloaded and in an uncompressed state. Under these conditions the check valve seal 406 maintains the seal against the interior wall of the barrel 402, as shown in FIG. 7.

Figure 8:
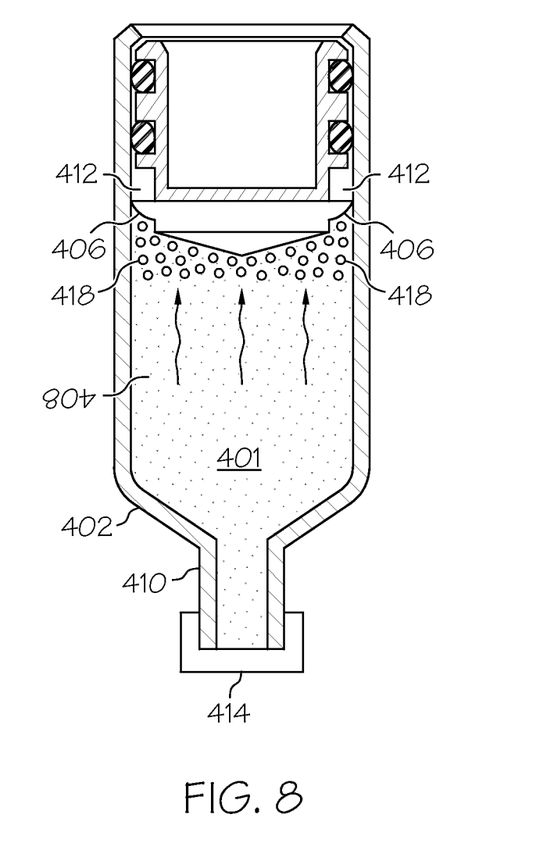

Air or other gas might be introduced into the liquid during the filling process. Moreover, some of this gas can be trapped inside the barrel 402 after securing the sealing cap 414 in place. In this regard, FIG. 7 schematically depicts gas bubbles 418 dispersed throughout the liquid 401 inside the barrel 402. The manufacturing process may continue by inverting the syringe assembly 400 and maintaining it in a position that allows gas in the main fluid chamber to accumulate and rise toward the piston 404 (see FIG. 8). In practice, the syringe assembly 400 should be held in an upright (vertical) position with the check valve seal 406 above the sealing cap 414, to allow the gas bubbles 418 in the liquid 401 to rise, accumulate, and settle at or near the check valve seal 406. The wavy arrows in FIG. 8 represent the rising and settling of the gas near the check valve seal 406. Depending upon the specific manufacturing procedure, the syringe assembly 400 may be held in the settling position without applying any additional stimuli. Alternatively, it may be desirable to accelerate the settling of the gas (if possible) by gently agitating the syringe assembly 400, by changing the surrounding temperature, or the like.

Figure 9A:
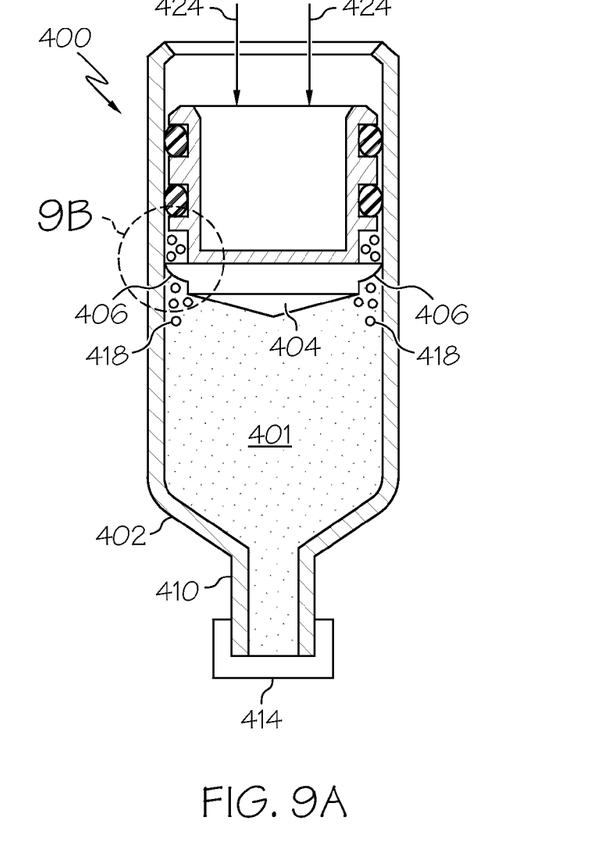
Figure 9B:
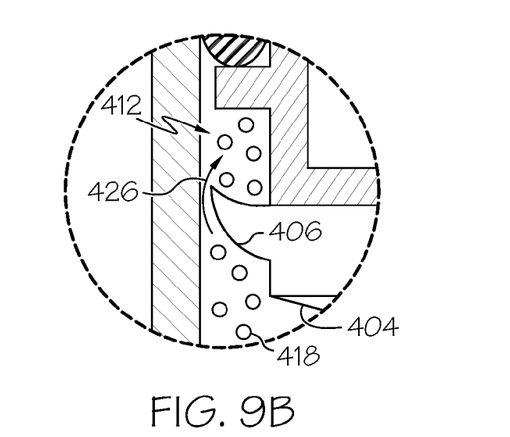

After the gas in the barrel 402 has settled at the check valve seal 406, an actuation force is applied to the piston 404 (while maintaining the syringe assembly 400 in its inverted position). The arrows 424 in FIG. 9 represent the actuation force. The actuation force 424 causes the piston 404 to slightly move into the barrel 402 toward the sealing cap 414, as depicted in FIG. 9. The compression of the piston 404 at this time causes the check valve seal 406 to temporarily disengage from the interior wall of the barrel, as shown in the detail section of FIG. 9. Note that disengagement of the check valve seal 406 in this manner occurs because the barrel 402 and the main fluid chamber are sealed and the piston is loaded under a compressive force. Under these conditions, the check valve seal 406 allows the gas to flow from the main fluid chamber into the fluid entrapment zone 412. The arrow 426 in the detail section of FIG. 9 indicates the flow path of the gas past the check valve seal 406. The piston 404 can be moved into the barrel 402 as far as needed to entrap the desired amount of gas within the fluid entrapment zone 412.

Figure 10:
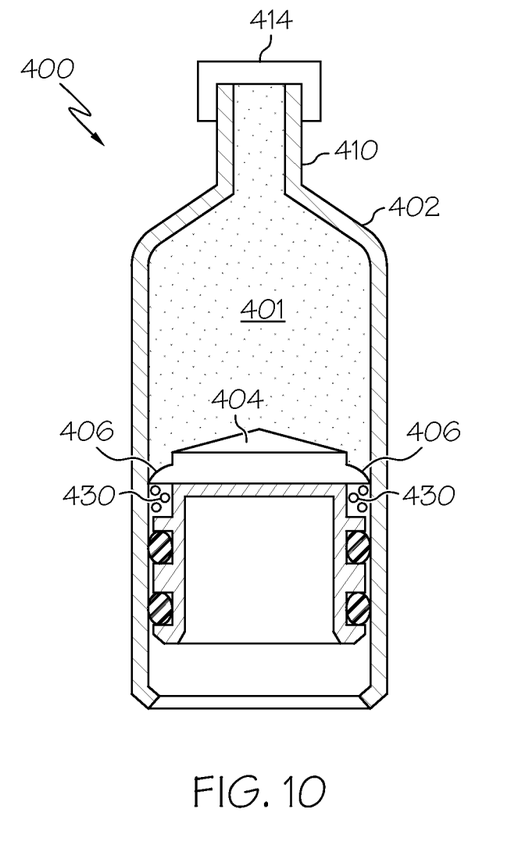

After the desired amount of gas flows past the check valve seal 406 and into the fluid entrapment zone 412, the actuation force 424 is removed from the piston 404 to return the check valve seal 406 to its nominal and unbiased state. FIG. 10 depicts the syringe assembly after removal of the actuation force 424. In this state the check valve seal 406 retains the captured gas 430 in the fluid entrapment zone 412. At this time, manufacturing of the syringe assembly 400 can be completed as desired. The check valve seal 406 is suitably configured to maintain the captured gas 430 in the fluid entrapment zone 412 while fabrication of the syringe assembly 400 is completed, during packaging, shipping, and storage of the syringe assembly 400, and during user manipulation and installation of the syringe assembly 400. In this regard, the captured gas 430 should remain in the fluid entrapment zone 412 after the syringe assembly 400 is installed in a fluid infusion device (see FIG. 3). Moreover, the captured gas 430 remains in the fluid entrapment zone 412 after the syringe assembly 400 has been opened (unsealed) for purposes of dispensing fluid. In particular, the check valve seal 406 maintains its seal against the interior wall of the barrel 402 when the main fluid chamber is unsealed (e.g., the sealing cap 414 has been penetrated), and when the piston is compressed for purposes of delivering the liquid out of the barrel 402.

Accordingly, the check valve seals described above can be utilized with a piston of a fluid reservoir such that the reservoir can be pre-filled in an easy and cost efficient manner without performing time consuming and complicated procedures intended to completely eliminate the presence of gas or air during filling. Rather, the check valve seals allow a manufacturer of pre-filled reservoirs to tolerate and accommodate some amount of gas that might be trapped inside the sealed reservoirs. The check valve seals, along with the manufacturing procedure described above, can be used to collect and capture the trapped gas without having to perform a post-fill venting or priming operation.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A fluid syringe comprising:
   a syringe barrel comprising an interior wall and a sealed main fluid chamber;
   a syringe piston slidably coupled within the syringe barrel, the syringe piston comprising a piston seal forming an interference fluid seal against the interior wall; and
   a check valve seal coupled to the syringe piston and located between the piston seal and the main fluid chamber, the check valve seal forming an interference fluid seal against the interior wall when the syringe piston is unloaded, and the check valve seal disengaging the interior wall to allow gas flow from the main fluid chamber toward the piston seal when the syringe piston is loaded.

2. The fluid syringe of claim 1, wherein the check valve seal forms an interference fluid seal against the interior wall when the syringe barrel is unsealed and the syringe piston is loaded for purposes of dispensing fluid.

3. The fluid syringe of claim 1, wherein the syringe piston comprises a piston body having a fluid end near the main fluid chamber, and having an actuator end opposite the fluid end, wherein:
   the piston seal is coupled to the piston body and located between the fluid end and the actuator end; and
   the check valve seal is coupled to the piston body and positioned such that the piston seal is located between the check valve seal and the actuator end.

4. The fluid syringe of claim 1, further comprising a liquid medication within the sealed main fluid chamber.

5. The fluid syringe of claim 4, wherein the liquid medication comprises insulin.

6. The fluid syringe of claim 4, further comprising a gas entrapment zone defined between the check valve seal, the piston seal, and the interior wall, wherein the check valve seal allows gas trapped in the main fluid chamber to flow into the gas entrapment zone when the syringe piston is loaded.

7. The fluid syringe of claim 6, wherein the check valve seal inhibits gas flow from the gas entrapment zone into the main fluid chamber.

8. The fluid syringe of claim 1, wherein the syringe piston further comprises an end seal forming an interference fluid seal against the interior wall, wherein the piston seal is located between the check valve seal and the end seal.

9. The fluid syringe of claim 8, wherein the piston seal inhibits gas flow from the gas entrapment zone toward the end seal.

10. The fluid syringe of claim 1, wherein:
    the piston seal is formed from a first resilient material having a first durometer; and
    the check valve seal is formed from a second resilient material having a second durometer that is equal to the first durometer.

\* \* \* \* \*